(12) United States Patent
Bommarito et al.

(10) Patent No.: US 12,263,268 B2
(45) Date of Patent: Apr. 1, 2025

(54) STERILIZATION TEST PACK

(71) Applicant: Solventum Intellectual Properties Company, Maplewood, MN (US)

(72) Inventors: G. Marco Bommarito, Stillwater, MN (US); Timothy J. Nies, Stillwater, MN (US); Michael J. Woodson, West St. Paul, MN (US); Andrew K. Hartzell, Hudson, WI (US); Joshua D. Erickson, Blaine, MN (US); Jonathan C. Fuller, Oakdale, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 762 days.

(21) Appl. No.: 17/594,637

(22) PCT Filed: Apr. 10, 2020

(86) PCT No.: PCT/IB2020/053453
§ 371 (c)(1),
(2) Date: Oct. 25, 2021

(87) PCT Pub. No.: WO2020/222054
PCT Pub. Date: Nov. 5, 2020

(65) Prior Publication Data
US 2022/0249725 A1     Aug. 11, 2022

Related U.S. Application Data

(60) Provisional application No. 62/842,218, filed on May 2, 2019.

(51) Int. Cl.
*A61L 2/28* (2006.01)
*A61L 2/07* (2006.01)
*A61L 2/20* (2006.01)

(52) U.S. Cl.
CPC .................. *A61L 2/28* (2013.01);
*A61L 2/07* (2013.01); *A61L 2/206* (2013.01);
*A61L 2/208* (2013.01);
(Continued)

(58) Field of Classification Search
CPC ..... A61L 2/00; A61L 2/02; A61L 2/04; A61L 2/06; A61L 2/07; A61L 2/16; A61L 2/20;
(Continued)

(56) References Cited

U.S. PATENT DOCUMENTS 5,204,062 A    4/1993  Buglino
5,514,120 A    5/1996  Johnston
(Continued)

FOREIGN PATENT DOCUMENTS

EP    0421760    4/1991
EP    1308175    5/2003
(Continued)

OTHER PUBLICATIONS

International Search report for PCT International Application No. PCT/IB2020/053453 mailed on Jul. 14, 2020, 4 pages.

*Primary Examiner* — Natasha E Young

(57) ABSTRACT

A sterilization test pack may include a shell defining an indicator compartment having a volume; a channel extending between a compartment opening and an exterior opening, the channel being in fluid communication with the indicator compartment through the compartment opening and surrounding atmosphere being in fluid communication with the channel through the exterior opening such that the indicator compartment is in fluid communication with the surrounding atmosphere through the channel, the channel having a length measured between the compartment opening and the exterior opening and a hydraulic radius along the length; and an indicator disposed in the indicator compartment, where a ratio of the compartment volume to the (Continued)

channel hydraulic radius may range from 1000 cm² to 8000 cm².

20 Claims, 7 Drawing Sheets

(52) U.S. Cl.
CPC ..... *A61L 2202/122* (2013.01); *A61L 2202/24* (2013.01)

(58) Field of Classification Search
CPC . A61L 2/206; A61L 2/208; A61L 2/26; A61L 2/28; A61L 2202/00; A61L 2202/10; A61L 2202/12; A61L 2202/122; A61L 2202/20; A61L 2202/24; A61L 2202/26; G01N 31/00; G01N 31/22; G01N 31/226
See application file for complete search history.

(56) References Cited

U.S. PATENT DOCUMENTS

| | | |
|---|---|---|
| 5,725,446 A | 3/1998 | Kaku |
| 5,728,446 A | 3/1998 | Johnston |
| 7,045,343 B2 * | 5/2006 | Witcher .............. A61L 2/28 435/31 |
| 9,017,994 B2 * | 4/2015 | Franciskovich ........ C12Q 1/22 422/417 |
| 2003/0190253 A1 | 10/2003 | Kohler et al. |
| 2003/0215923 A1 | 11/2003 | Witcher |
| 2008/0261296 A1 | 10/2008 | Justi |
| 2009/0028752 A1 | 1/2009 | Bala |
| 2017/0184444 A1 | 6/2017 | Yumoto |
| 2017/0211035 A1 | 7/2017 | Yirava et al. |
| 2018/0187143 A1 | 7/2018 | Yirava et al. |

FOREIGN PATENT DOCUMENTS

| | | |
|---|---|---|
| WO | WO 1999-062569 | 12/1999 |
| WO | WO 2001-056618 | 8/2001 |
| WO | 2004084956 A1 | 10/2004 |
| WO | 2013122852 A1 | 8/2013 |
| WO | WO 2017-184444 | 10/2017 |

* cited by examiner

STERILIZATION TEST PACK

CROSS REFERENCE TO RELATED APPLICATIONS

This application is a national stage filing under 35 U.S.C. 371 of PCT/IB2020/053453, now WO 2020/222054, filed Apr. 10, 2020, which claims the benefit of Provisional Application No. 62/842,218, filed May 2, 2019, the disclosure of which is incorporated by reference in its/their entirety herein.

FIELD

The present disclosure relates to test packs that can be used to monitor and test the effectiveness of sterilization. In particular, the present disclosure relates to test packs that can be used to monitor and test the effectiveness of steam sterilization.

BACKGROUND

In sterilization processes, sterilant gases like steam, hydrogen peroxide, or ethylene oxide, may be used to sterilize a load. The load may include items such as garments, tools, and instruments. Monitoring sterilization processes generally involves running chemical and/or biological indicators alongside each load being sterilized. The indicators can either be placed with instruments within each wrapped tray, or they can be processed in a separate process challenge device.

Process challenge devices are designed to simulate the resistance to sterilant penetration that is presented by the load or an item within the load, which is dependent on the load item's geometry and material, as well as the sterile packaging. When the sterilant adequately penetrates the process challenge device and sufficiently exposes the included biological and/or chemical indicators, it provides assurance of sterility for the other load items in the sterilizer chamber.

Biological indicators are used to gauge the effectiveness of the sterilization procedure by monitoring the survival of a test microorganism contained in the biological indicator. The test microorganism is selected such that it is many times more resistant to the sterilization process than most organisms. In order to test the effectiveness of the sterilization cycle, the biological indicator is placed in the sterilizer for the duration of the cycle. After the sterilization cycle, the biological indicator is removed and incubated under conditions that will promote the growth of any surviving test microorganisms. If the sterilization cycle failed, surviving microorganisms in the biological indicator generate a detectable signal indicating that the sterilization cycle was not effective.

Chemical indicators include one or more chemical components that react to a particular condition, such as the presence of a particular chemical or a temperature for a certain period of time. Chemical indicators can be read immediately at the end of the sterilization process. The results indicate only whether the condition was present during the sterilization process.

One process control device commonly used in hospitals today is the ATTEST™ Rapid 5 Steam Plus Test Pack available from 3M Company in Maplewood, MN. The Rapid 5 pack includes a stack of paper medical index cards and an indicator embedded in a die-cut cavity in the stack. The stacked cards are overwrapped with a sterilization wrap and secured with an adhesive label. The Rapid 5 process control device is constructed to match the performance of the AAMI (Association for the Advancement of Medical Instrumentation) 16-towel pack, an industry standard which is primarily a porous and absorbent load type.

SUMMARY

The present disclosure relates to test packs that can be used to monitor and test the effectiveness of sterilization. In particular, the present disclosure relates to test packs that can be used to monitor and test the effectiveness of steam sterilization.

According to one embodiment, the sterilization test pack may include a shell defining an indicator compartment having a volume; a channel extending between a compartment opening and an exterior opening, the channel being in fluid communication with the indicator compartment through the compartment opening and surrounding atmosphere being in fluid communication with the channel through the exterior opening such that the indicator compartment is in fluid communication with the surrounding atmosphere through the channel, the channel having a length measured between the compartment opening and the exterior opening and a hydraulic radius along the length; and an indicator disposed in the indicator compartment, where a ratio of the compartment volume to the channel hydraulic radius is from 1000 $cm^2$ to 8000 $cm^2$.

According to one embodiment, the sterilization test pack may include a shell defining an indicator compartment having a volume; a channel extending between a compartment opening and an exterior opening, the channel being in fluid communication with the indicator compartment through the compartment opening and surrounding atmosphere being in fluid communication with the channel through the exterior opening such that the indicator compartment is in fluid communication with the surrounding atmosphere through the channel, the channel having a length measured between the compartment opening and the exterior opening and a hydraulic radius along the length; and an indicator disposed in the indicator compartment, where the sterilization test pack exhibits a diffusivity ($L_D$) of 0.02 cm to 60 cm or less.

According to one embodiment, the sterilization test pack may include a shell defining an indicator compartment having a volume of 15 $cm^3$ to 300 $cm^3$; a channel extending between a compartment opening and an exterior opening, the channel being in fluid communication with the indicator compartment through the compartment opening and surrounding atmosphere being in fluid communication with the channel through the exterior opening such that the indicator compartment is in fluid communication with the surrounding atmosphere through the channel, the channel having a length of 30 mm to 1000 mm measured between the compartment opening and the exterior opening, and a maximum hydraulic radius of 1.0 mm at any selected location along the length; and an indicator disposed in the indicator compartment.

The term "sterilant" is used in this disclosure to describe a substance used during a sterilization process to kill microorganisms. The substance is typically gaseous under the sterilizing conditions. Examples of sterilants include steam, hydrogen peroxide, and ethylene oxide.

The term "flexural modulus" is used in this disclosure to refer to the tendency of a material to resist bending. Flexural modulus can be measured using ASTM D790.

The term "heat deflection temperature" is used in this disclosure to refer to the temperature at which a polymer or plastic deforms under a specified load of 66 psi. Heat deflection temperature can be measured using ASTM D648.

The term "hydraulic radius" is defined as the cross-sectional area of flow in the channel divided by the wetted perimeter of the channel Calculation of the hydraulic radius of the channel (at a selected location) can be represented by the following equation: hydraulic radius=(2×area of channel)/(perimeter of channel).

The terms "integral" and "integrally formed" are used in this disclosure to describe elements that are formed in one piece (a single, unitary piece) and cannot be separably removed from each other without causing permanent structural damage to the piece.

The term "transparent" is used in this disclosure to describe a material that can be seen through with a naked eye. A transparent material transmits at least 90% of electromagnetic radiation having wavelengths in the visible spectrum (e.g., from about 380 nm to about 740 nm). A transparent material may be colorless or colored.

The term "opaque" is used in this disclosure to describe materials that do not allow visible light to pass through. An opaque material transmits less than 10% of electromagnetic radiation having wavelengths in the visible spectrum (e.g., from about 380 nm to about 740 nm). An opaque material may be colorless or colored.

The term "semi-transparent" is used in this disclosure to describe a material quality that is between opaque and transparent. For example, it may be possible to see a liquid level through a semi-transparent wall of a container.

The terms "plastic," "polymer" and "polymeric material" refer to materials prepared from one monomer, such as a homopolymer, and to materials prepared from two or more monomers, such as a copolymer, terpolymer, or the like.

The term "pouch" refers to a pocket or bag shape that deforms to accommodate objects placed therein.

The term "substantially" as used here has the same meaning as "significantly," and can be understood to modify the term that follows by at least about 75%, at least about 90%, at least about 95%, or at least about 98%. The term "not substantially" as used here has the same meaning as "not significantly," and can be understood to have the inverse meaning of "substantially," i.e., modifying the term that follows by not more than 25%, not more than 10%, not more than 5%, or not more than 2%.

The term "about" is used here in conjunction with numeric values to include normal variations in measurements as expected by persons skilled in the art and is understood have the same meaning as "approximately" and to cover a typical margin of error, such as ±5% of the stated value.

Terms such as "a," "an," and "the" are not intended to refer to only a singular entity but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" or "at least" a particular value, that value is included within the range.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

DETAILED DESCRIPTION

The present disclosure relates to sterilization test packs useful for testing the effectiveness of a sterilization procedure. The sterilization test packs can be broadly categorized as "lumen-challenge" test packs.

The performance of sterilization test packs may be compared against a so-called towel test pack. The towel test pack includes a stack of surgical towels and an indicator embedded in the stack. While historically the AAMI 16-towel pack has proven to be one of the most challenging items to sterilize, advancements in medical instrumentation have created even more challenging items to be sterilized.

It is common for medical instruments to include parts that have a cavity or a lumen. Sterilizing such instruments is more challenging than other instruments because the sterilant has to reach through the entire cavity or lumen during the sterilization process. Typical sterilization test packs of the AAMI 16-towel pack are not able to adequately test or monitor sterilization of long lumens. It would, therefore, be desirable to provide a sterilization test pack that more accurately models sterilization of instruments with a cavity or lumen.

A lumen-challenge test pack provides an increased resistance against the sterilant to simulate a situation where an item with a lumen (e.g., a medical instrument) is placed in the sterilizer and the sterilization cycle is used to kill microorganisms inside the lumen. The test pack generally includes a shell defining an indicator compartment for holding a sterilization indicator, a sterilization indicator, and a lid. During a sterilization procedure, sterilant may enter the test pack through the lumen path and contact the sterilization indicator. The challenge to the sterilant penetration is provided by the lumen channel and an indicator cavity volume.

Figure 1A:
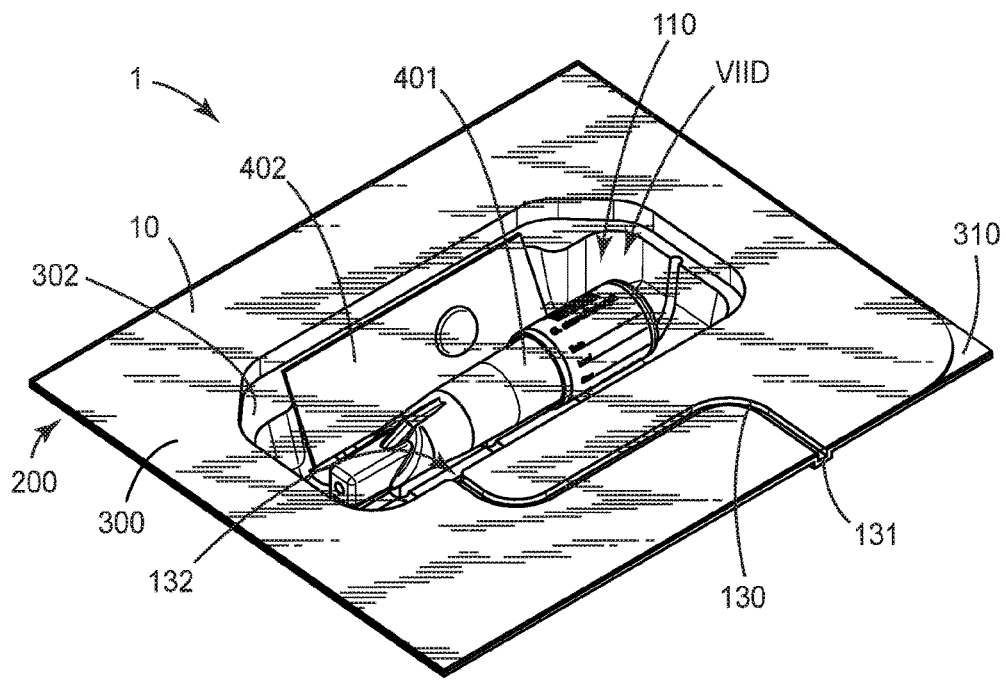
FIG. 1A is a perspective view of a sterilization test pack according to an embodiment.

FIG. 1A depicts one illustrative embodiment of a sterilization test pack 1. The sterilization test pack 1 includes a shell 10 formed by a bottom portion 200 and a top portion or cover 300. The shell 10 defines an indicator compartment 110 having a volume V110 constructed or configured to house an indicator, such as a biological indicator 401, a chemical indicator 402, or both. The shell forms a channel 130 (e.g., lumen) that extends between a compartment opening 132 and an exterior opening 131. The channel 130 is in fluid communication with the indicator compartment 110 through the compartment opening 132, and with the surrounding atmosphere through the exterior opening 131, such that the channel 130 provides fluid communication between the indicator compartment 110 and the surrounding atmosphere (e.g., the sterilizer chamber).

Generally, when the sterilization test pack 1 is in use, the test pack is placed onto a sterilization tray along with the load to be sterilized. The tray is then place in the sterilizer and a sterilization cycle is initiated. During the sterilization cycle, sterilant (for example, pressurized steam) enters the channel 130 (e.g., lumen) of the sterilization test pack 1 through the exterior opening 131. The geometry of the channel 130 and the indicator compartment 110 is designed such that it provides suitable resistance to the sterilant and simulates the resistance to sterilant penetration that is presented by the load. Examples of parameters that influence sterilant resistance include the length, hydraulic radius, and volume of the channel, and the volume of the indicator compartment. Indicators included in the indicator compartment indicate if the sterilization cycle was successful (e.g., the sterilant successfully entered the indicator compartment and sufficiently exposed the included biological and/or chemical indicators to the sterilant).

The indicators may include a biological indicator 401 that can be used to monitor the survival of a test microorganism contained in the biological indicator. After the sterilization cycle, the biological indicator is removed and incubated under conditions that will promote the growth of any surviving test microorganisms. If the sterilization cycle failed, surviving microorganisms in the biological indicator generate a detectable signal indicating that the sterilization cycle was not effective.

The indicators may include a chemical indicator 402 that can be used to monitor the presence of a particular condition, such as the presence of a particular chemical or a temperature for a certain period of time. Chemical indicators can be read immediately at the end of the sterilization process to see whether the condition was present during the sterilization process.

Figure 1B:
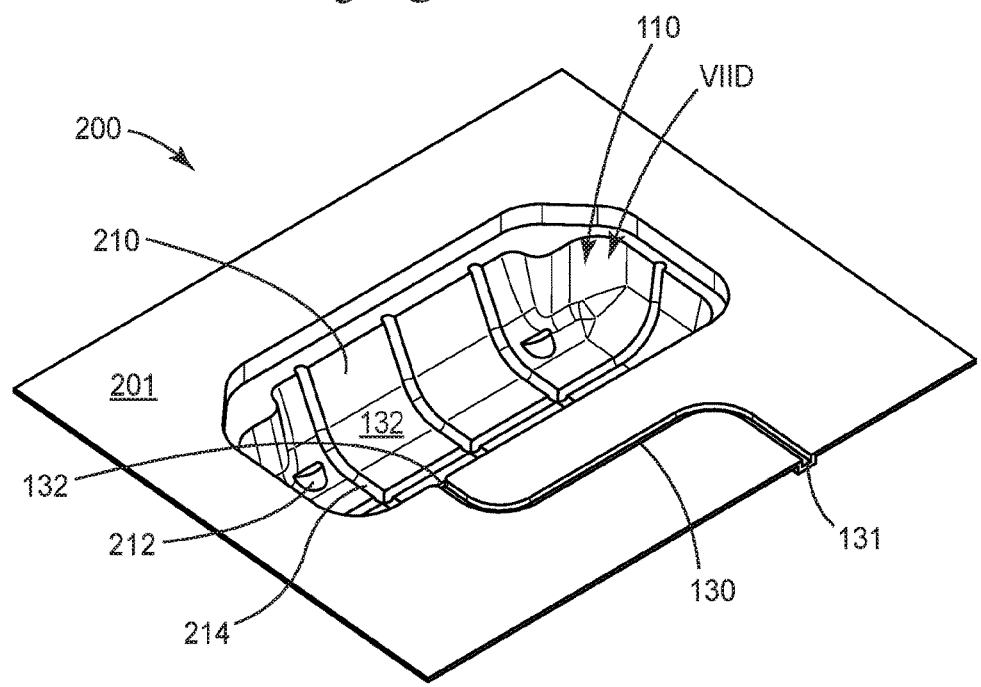
FIG. 1B is a perspective view of the bottom portion of the sterilization pack of FIG. 1A.
Figure 1C:
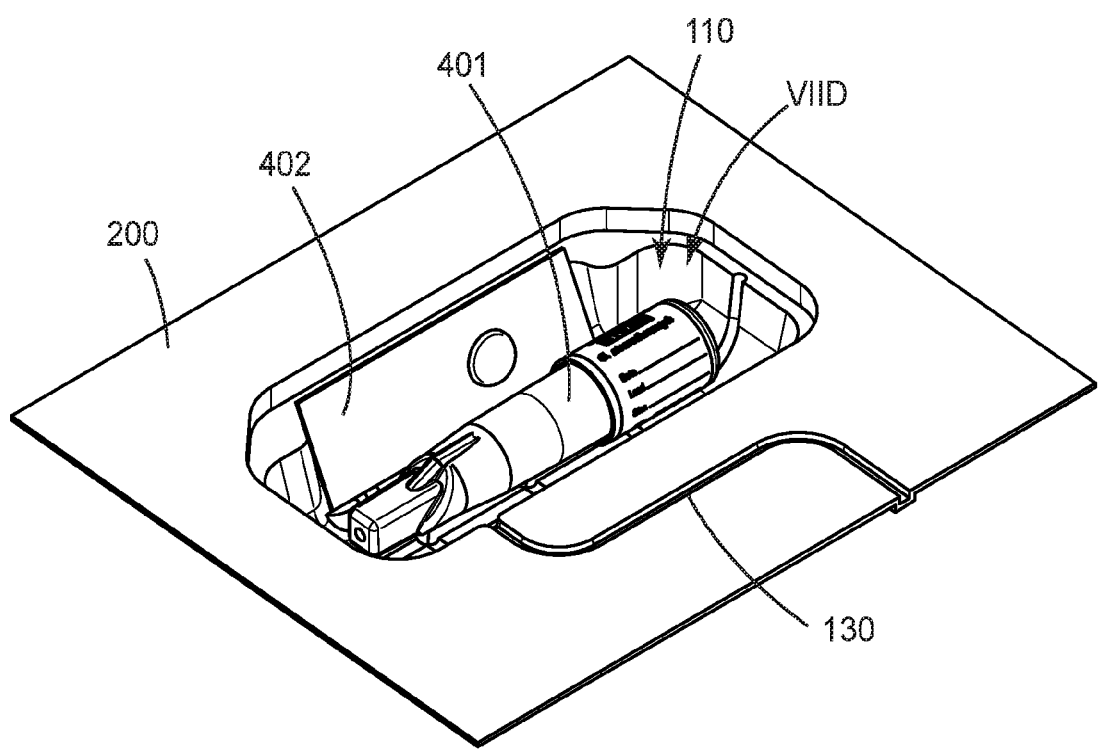
FIG. 1C is a perspective view of the bottom portion of the sterilization pack of FIG. 1A with indicators.
Figure 2A:
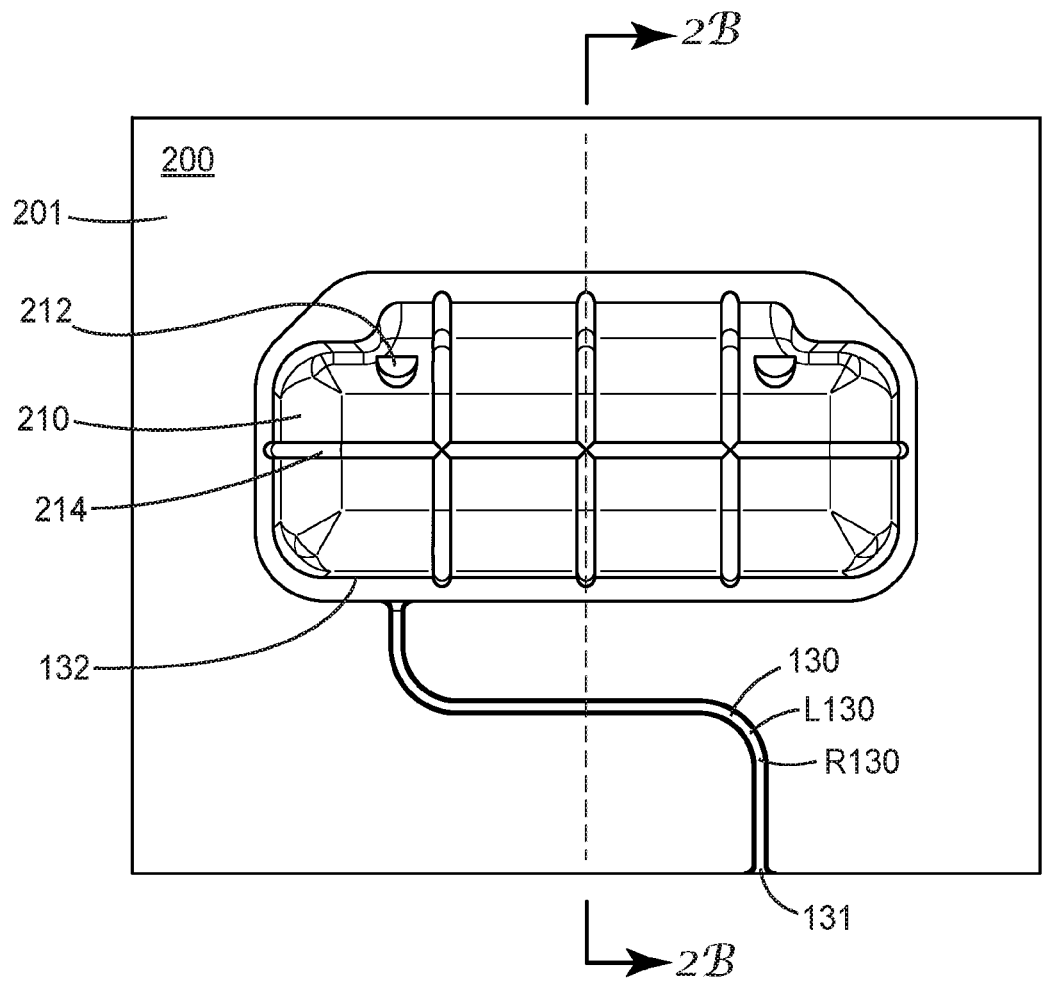
FIG. 2A is a top view of the bottom portion of the sterilization pack of FIG. 1A.
Figure 2B:
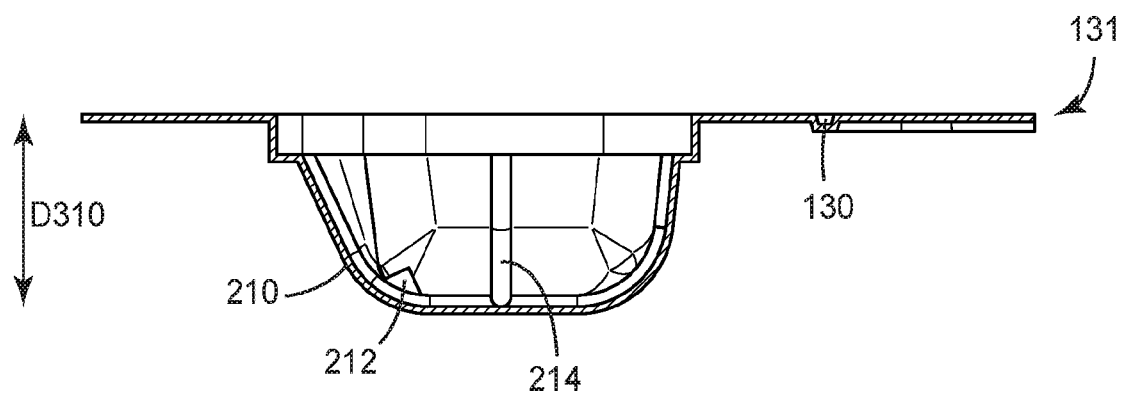
FIG. 2B is a cross-sectional side view of the bottom portion of the sterilization pack of FIG. 1A.

FIG. 1B is a perspective view of the bottom portion 200 of the shell 10 without indicators. FIG. 1C is a perspective view of the bottom portion 200 of the shell 10 with the indicators. FIGS. 2A and 2B show a top view and a cross-sectional view of the bottom portion 200, respectively. According to one embodiment, the bottom portion 200 forms a bottom wall 210 forming the indicator compartment 110. For example, the bottom wall 210 may define a self-supporting cup that forms the indicator compartment 110. The indicator compartment 110 may be sized to accommodate one or more indicators, such as a biological indicator 401, a chemical indicator 402, or both. The indicator compartment 110 may further be sized to provide a suitable back pressure to sterilant entering the sterilization test pack 1 through the channel 130.

The indicator compartment 110 may have a volume V110 and a depth D110. The volume V110 may be 15 cm$^3$ (cubic centimeters, also equal to milliliters, mL) or greater, 20 cm$^3$ or greater, 30 cm$^3$ or greater, 40 cm$^3$ or greater, 50 cm$^3$ or greater, 60 cm$^3$ or greater, 80 cm$^3$ or greater, or 100 cm$^3$ or greater. The volume V110 may be 300 cm$^3$ or less, 250 cm$^3$ or less, 200 cm$^3$ or less, 150 cm$^3$ or less, 130 cm$^3$ or less, 120 cm$^3$ or less, or 110 cm$^3$ or less. In some embodiments, the volume V110 ranges from 25 cm$^3$ to 200 cm$^3$, or from 40 cm$^3$ to 125 cm$^3$. The depth D110 may be 15 mm or greater, 20 mm or greater, or 25 mm or greater. The depth D110 may be 100 mm or less, 70 mm or less, 50 mm or less, or 40 mm or less. In some embodiments, the depth D110 ranges from 15 mm to 70 mm, or from 20 mm to 50 mm.

Figure 3A:
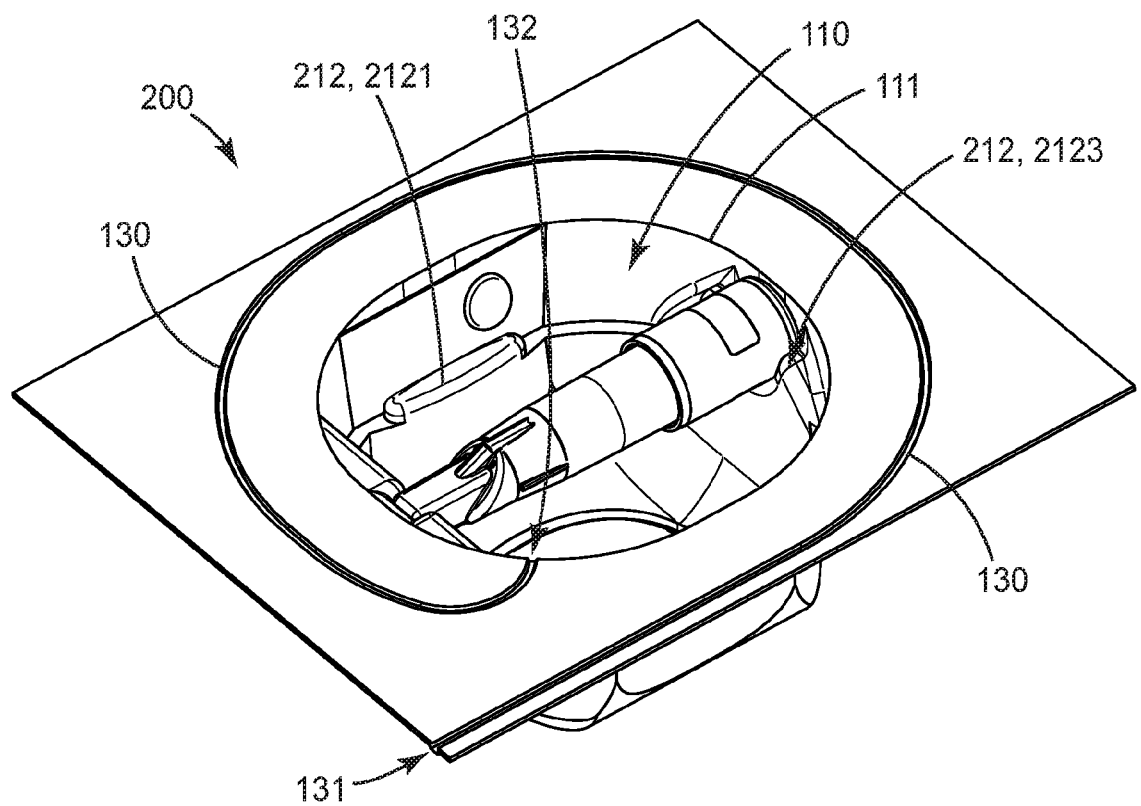
FIG. 3A is a perspective view of the bottom portion of a sterilization test pack according to an embodiment.
Figure 3B:
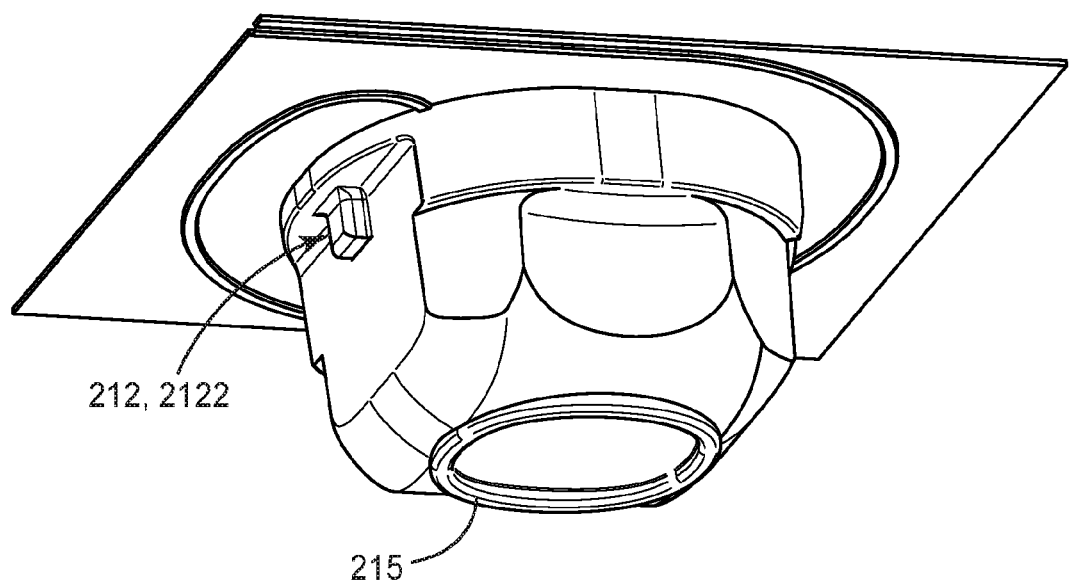
FIG. 3B is a perspective view of the bottom portion of the sterilization pack of FIG. 3A.

The bottom wall 210 may include features that facilitate placement or orientation of, and/or immobilize the indicators in the indicator compartment 110. For example, the bottom wall 210 may include one or more indicator support structures 212 constructed or configured to receive one or more indicators. In FIGS. 1A-2C, the indicator support structures 212 include protrusions that facilitate placement or orientation of, and/or immobilize the chemical indicator 402. In FIGS. 3A and 3B, the indicator support structures 212 include a lip 2121 that facilitates placement or orientation of, and/or immobilizes the chemical indicator 402, and pockets 2122, 2123 that facilitate placement or orientation of, and/or immobilize the biological indicator 401.

The bottom wall 210 may include features that provide rigidity and/or stability to the sterilization test pack 1. For example, the bottom wall 210 may include one or more reinforcing structures (e.g., ribs) 214 (FIGS. 2A and 2B), 215 (FIG. 3B).

The bottom portion 200 may also include a flat portion 201 substantially surrounding the bottom wall 210. The flat portion 201 may be planar or substantially planar. The flat portion 201 may facilitate attaching the top portion 300 to the bottom portion. For example, the top portion 300 may be adhered to the flat portion 201. The top portion 300 and bottom portion 200 may be sealingly coupled around the indicator compartment 110 outside of the channel 130. This may be achieved by adhering the top portion 300 to the flat portion 201 only. When the test pack is assembled, the top portion 300 may be flat or substantially flat.

In some embodiments, the top portion 300 is removable from the bottom portion 200 without the use of tools. For example, the top portion 300 may be peelable. The top portion 300 may include a tab 310 or other feature to facilitate toolless removal.

The bottom portion 200 may also define the channel 130 extending across the flat portion 201 from the compartment opening 132 to the exterior opening 131. Alternatively, the channel 130 may be formed by the top portion 300. The channel 130 has a length L130 and a hydraulic radius R130 measured anywhere along the length L130.

Figure 4:
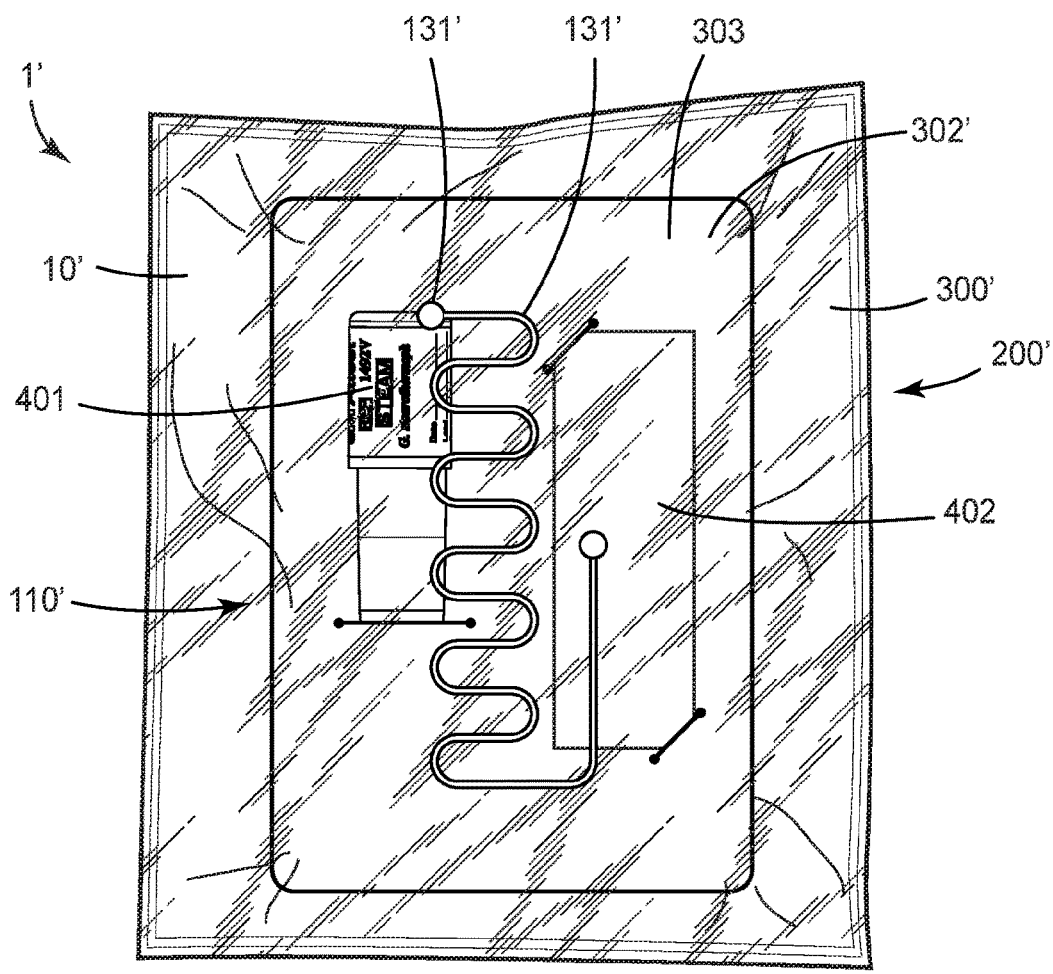
FIG. 4 is a top view of a sterilization test pack according to an embodiment.

An alternative embodiment of the sterilization test pack 1' is shown in FIG. 4. The test pack 1 may have a bag or pouch-like shape formed from polymeric sheets or films or other suitable materials. The sterilization test pack 1' has a shell 10' formed by a bottom portion 200' and a top portion or cover 300'. The interior of the shell 10' defines the indicator compartment 110', which may include one or more indicators, such as a biological indicator 401 and/or a chemical indicator 402. The indicator compartment 110' has a volume V110'.

The sterilization test pack 1' includes laminated or layered sheets shown in FIGS. 5A-5D. The sheets form at least a part of the shell 10' of the test pack 1'. The sheets further form the channel 130' (e.g., lumen) that extends between a compartment opening 132' and an exterior opening 131'.

Figure 5A:
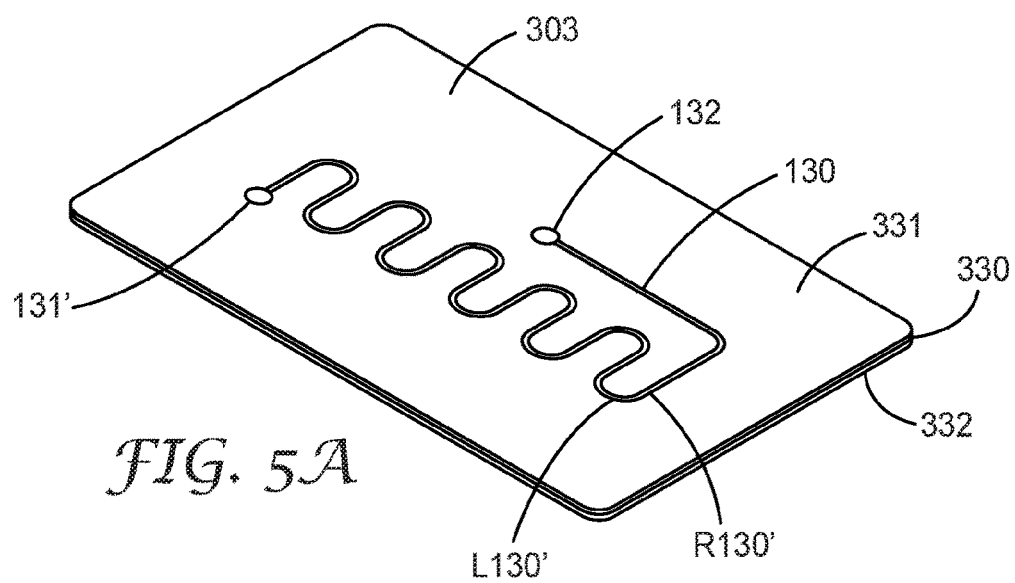
FIG. 5A is a perspective view of a layered structure of the sterilization pack of FIG. 4.
Figure 5D:
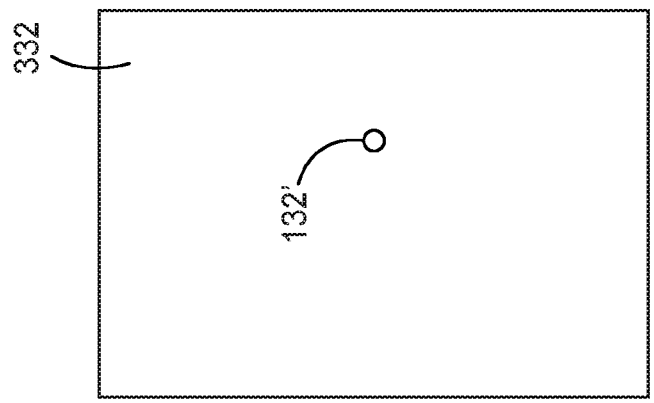
FIG. 5D is a top view of a bottom layer of layered structure pack of FIG. 5A.
Figure 5C:
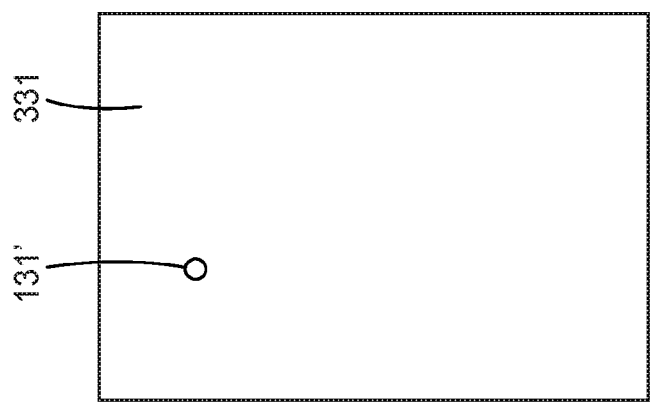
FIG. 5C is a top view of a top layer the layered structure of FIG. 5A.
Figure 5B:
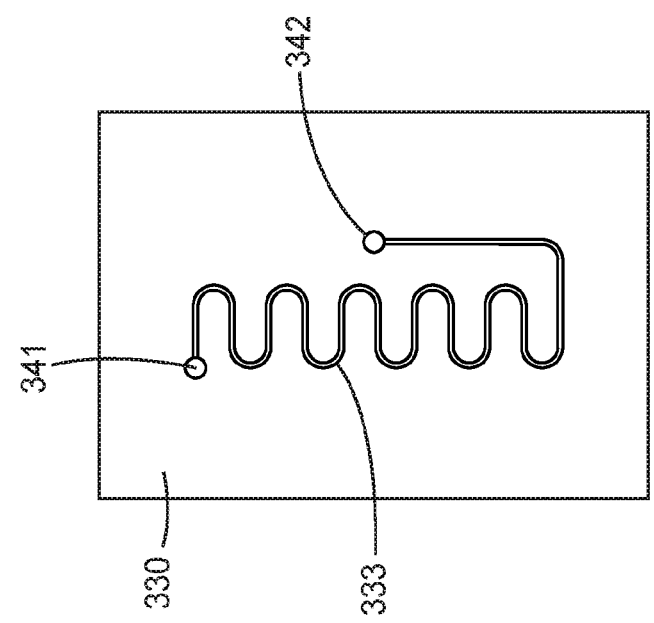
FIG. 5B is a top view of a middle layer of the layered structure of FIG. 5A.

The layered sheets include a three-layer laminate 303 shown in FIG. 5A. The three-layer laminate 303 includes a lumen layer 330 sandwiched between a top layer 331 and a bottom layer 332. The lumen layer 330 has an open lumen path 333 extending from a first end 341 to a second end 342 (see FIG. 5B). When the lumen layer 330 is laminated between the top layer 331 and the bottom layer 332, the open lumen path 333 forms the channel 130'. The channel 130' has a length L130' and a hydraulic radius R130' along the length L130'. The top layer 331 (see FIG. 5C) has an opening 131', which aligns with the first end 341 of the lumen path 333 and forms the exterior opening 131' of the channel 130'. The bottom layer 332 (see FIG. 5D) has an opening 132', which aligns with the second end 342 of the lumen path 333 and forms the compartment opening 132' of the channel 130'.

The three-layer laminate 303 may form the top portion 300' or part of the top portion 300' of the shell 10'. Alternatively, the three-layer laminate 303 forms the bottom portion 200' or part of the bottom portion 200' of the shell 10'. The opposite portion (e.g., bottom portion 200' or top portion 300') may include a single layer or another laminated sheet. The top and bottom portions 300', 200' may be adhered or sealed together along their edges. The three-layer laminate 303 may be adhered to the top portion 300' or the bottom portion 200'. The shell 10' may include a tab, notch, perforation, or other feature to facilitate opening the shell 10' and removing the one or more indicators.

A similar laminated lumen construction (as the three-layer laminate 303) may be used to apply a lumen to a shell with a bottom portion that is a formed tray with a flat portion 302 surrounding an indicator compartment 110.

The following features apply to each of the various embodiments shown in the figures and discussed above unless otherwise stated.

In some embodiments, the channel has the same or substantially same cross section throughout its length. For example, the channel hydraulic radius R130 may have a minimum value and maximum value, where the maximum value is the same or up to 10% greater, up to 25% greater, or up to 50% greater than the minimum value. In such cases, the channel length L130 may be defined as the entire length of the channel 130 between the compartment opening 132 and the exterior opening 131. The hydraulic radius R130 may be determined anywhere along the channel length L130.

Figure 6:
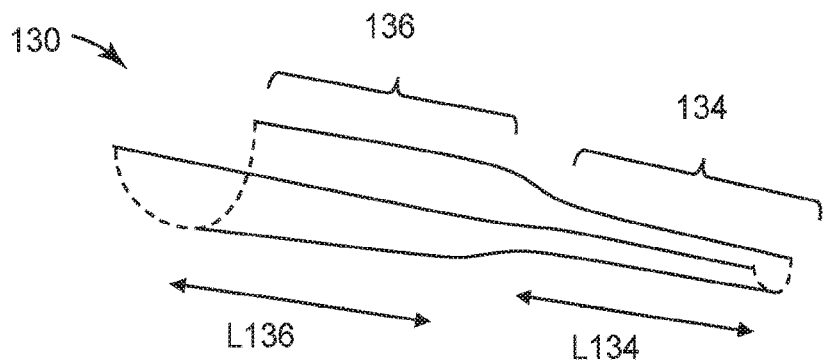
FIG. 6 is a schematic view of a portion of a channel in a sterilization test pack according to an embodiment.

In an alternative embodiment, the hydraulic radius R130 of the channel varies more significantly along the length of the channel. For example, the hydraulic radius R130 may have a minimum value defining a restricted portion 134, and a maximum value defining an enlarged portion 136, where the maximum value is at least 50% greater, at least 75% greater, or at least 100% greater than the minimum value. See FIG. 6. In such cases, the restricted portion 134 of the channel may be considered a lumen having a lumen length L134, and the enlarged portion 136 may have an enlarged channel length L136. For purposes of defining lumen challenge (e.g., diffusivity) for sterilant penetration, the values of the channel length 130 may be applied to the lumen length L134.

The dimensions of the test pack are selected to achieve desired indicator performance in a sterilization cycle. For example, the dimensions of the test pack are selected to achieve desired indicator performance in gravity steam sterilization cycles, dynamic-air-removal steam sterilization cycles, or both. The dimensions may include one or more of channel length, channel hydraulic radius, and indicator compartment volume. The dimensions may be interrelated such that for a certain indicator compartment volume, a suitable range of channel hydraulic radii may be selected. Further, for a certain indicator compartment volume, a suitable range of channel lengths may be selected.

The channel 130 may have a length L130 that is 30 mm or greater, 50 mm or greater, 100 mm or greater, 150 mm or greater, 200 mm or greater, 300 mm or greater, 400 mm or greater, or 500 mm or greater. The length L130 may be 1000 mm or less, 800 mm or less, 600 mm or less, 500 mm of less, 400 mm or less, or 300 mm or less. In some embodiments, the length L130 ranges from 30 mm to 600 mm, or from 50 mm to 400 mm.

The channel 130 may have a hydraulic radius R130 that is 0.10 mm or greater, 0.15 mm or greater, 0.17 mm or greater, 0.18 mm or greater, 0.19 mm or greater, or 0.20 mm or greater. The hydraulic radius R130 (e.g., the maximum hydraulic radius) may be 1.0 mm or less, 0.80 mm or less, 0.6 mm or less, 0.5 mm or less, 0.40 mm or less, or 0.35 mm or less. In some embodiments, the hydraulic radius R130 ranges from 0.15 mm to 0.50 mm, or from 0.18 mm to 0.40 mm.

In some embodiments, the indicator compartment volume V110 and the channel hydraulic radius R130 have a ratio V110:R130 of 500 cm$^2$ or greater, 800 cm$^2$ or greater, 1000 cm$^2$ or greater, 1200 cm$^2$ or greater, 1400 cm$^2$ or greater, 1500 cm$^2$ or greater, 1700 cm$^2$ or greater, or 2000 cm$^2$ or greater. The ratio V110:R130 may be 8000 cm$^2$ or less, 7000 cm$^2$ or less, 6500 cm$^2$ or less, 6000 cm$^2$ or less, or 5000 cm$^2$ or less. The ratio V110:R130 may range from 1000 cm$^2$ to 7000 cm$^2$ or from 1200 cm$^2$ to 6000 cm$^2$.

A channel cross sectional area A130 may also be calculated. In some embodiments, the indicator compartment volume V110 and the channel cross sectional area A130 have a ratio V110:A130 of 100 m or greater, 110 m or greater, 125 m or greater, 150 m or greater, 200 m or greater, 300 m or greater, or 400 m or greater. The ratio V110:A130 may be 1200 m or less, 1000 m or less, 800 m or less, or 600 m or less. The ratio V110:A130 may range from 100 cm to 1200 m or from 110 m to 1000 m.

The relationship between the dimensions indicator compartment volume V110, channel length L130, and channel hydraulic radius R130 may also be expressed as a diffusivity (or scaled diffusion length) $L_D$. Diffusivity can be calculated as:

$$L_D = \sqrt{\left\{ D + \left(\frac{r_h^3}{8\mu}\right)^2 \left(\frac{\Delta P}{L}\right)^2 \left(\frac{1}{48D}\right) \right\} t};$$

where
  D is saturated steam (vapor) diffusion constant;
  $r_h$ is hydraulic radius;
  μ is saturated steam (vapor) viscosity;

ΔP is pressure difference across the lumen;

L is length of the effective lumen (represents the length of the actual channel plus an additional length proportional to a lumen volume equal to the volume of the chamber and a hydraulic radius equivalent to that of the actual channel); and t is time.

In some embodiments, the sterilization test pack has a diffusivity $L_D$ of 0.02 cm or greater, 0.03 cm or greater, 0.05 cm or greater, 0.10 cm or greater, 0.20 cm or greater, 0.50 cm or greater, 1.0 cm or greater, 1.5 cm or greater, 2.0 cm or greater, 2.5 cm or greater, 3.0 cm or greater, 4.0 cm or greater, 5.0 cm or greater, 6.0 cm or greater, 8.0 cm or greater, 10 cm or greater, 12 cm or greater, 15 cm or greater, or 20 cm or greater. The diffusivity $L_D$ may be 60 cm or less, 50 cm or less, 40 cm or less, 35 cm or less, 30 cm or less, 25 cm or less, 20 cm or less, or 15 cm or less. The diffusivity $L_D$ may range from 0.03 cm to 40 cm, or from 0.10 cm to 30 cm.

The shape of the indicator compartment 110 and the path of the channel 130 are not particularly limited and may vary as shown, for example, in FIGS. 1A, 3A, and 4. The indicator compartment 110 may have a more rectangular or elongated shape as shown in FIG. 1A, or a more round or rounded square shape as shown in FIG. 3A. Other shapes are, of course, also possible. In the alternative embodiment shown in FIG. 4, the indicator compartment 110 assumes the shape of the inside of the bag.

The channel 130 may follow any suitable path to accommodate the length L130 of the channel 130. For example, the channel 130 may include straight sections, curved sections, or both, as shown in the figures. In one embodiment shown in FIGS. 3A and 3B, the channel 130 substantially surrounds the opening 111 of the indicator compartment 110. The shape of the cross-section of the channel 130 is not particularly limited and may be, for example, polygonal (e.g., triangular or quadrilateral, such as square or rectangular) or curved (e.g., arced, semicircular, or semi-oval).

The shell 10 of the sterilization test pack 1 can be formed by any suitable method. For example, the bottom portion 200 may be formed by thermo forming, injection molding, blow molding, machining, or a combination thereof. The bottom portion 200 may be formed as a single integral piece. The top portion 300 may be formed by extruding, laminating, or a combination thereof. The top portion 300 may be adhered to the bottom portion 200 (e.g., the flat portion 201) by an adhesive, heat bonding, or a combination thereof.

According to some embodiments, the shell 10 or a portion of the shell 10 is transparent or semi-transparent. For example, the top portion 300 and/or the bottom portion 200 may be transparent or semi-transparent or may include a transparent portion 302 or semi-transparent portion. The entire shell may also be prepared from a transparent or semi-transparent material such that the contents of the indicator compartment are visible from multiple angles. In some embodiments, the chemical indicator 402 is visible through the shell. In some embodiments, both the chemical indicator 402 and the biological indicator 401 are visible through the shell.

The bottom portion 200 and the top portion 300 may be prepared from any suitable material and may be made from the same or different materials. For example, in some embodiments the bottom portion 200 may be prepared from a polymeric material, such as polypropylene, polyethylene, polyethylene terephthalate (PET), polycarbonate, polyolefin, polystyrene, polyacrylamide, polymethacrylate, poly(methyl)methacrylate, polyimide, polyester, polyethylene, terephthalate, polybutylene terephthalate, polyvinylchloride, or a copolymer or a mixture thereof. In some embodiments, the top portion 300 may be prepared from a polymeric material, such as polypropylene, polyethylene, polyethylene terephthalate (PET), mylar, metal foil, polyester, polyolefin, polycarbonate, polyolefin, polystyrene, polyacrylamide, polymethacrylate, poly(methyl)methacrylate, polyimide, polyester, polyethylene terephthalate, polybutylene terephthalate, polyvinylchloride, or a combination thereof. In some embodiments, the bottom portion 200 and/or the top portion 300 may include glass, ceramic, metal, or a combination thereof. For example, the top portion 300 may be prepared from a polymeric material combined with another material, such as a polymeric film co-extruded or laminated onto a metallic film.

The sterilization test pack 1 may be constructed or configured to have a desired level of rigidity to withstand sterilization conditions. For example, the bottom portion 200 may be prepared from a polymeric material having a suitable thickness to provide a rigid or semi-rigid structure. The polymeric material of the bottom portion may have a flexural modulus in the range of 500 MPa to 2500 MPa and a heat deflection temperature greater than 160° F. The material and thickness may be selected so that a suitable rigidity is achieved for the test pack as a whole. For example, in some embodiments the bottom portion 200 is prepared from polypropylene having a wall thickness of 0.50 mm or greater, or 0.70 mm or greater, and 3.0 mm or less, 2.0 mm or less, or 1.0 mm or less.

In the bag-like embodiment shown in FIG. 4, the shell 10' may be prepared from a suitable film and may include polymeric materials and optionally metal (e.g., a metalized polymer film). In some embodiments, the bottom portion 200', the top portion 300', or both are prepared from polyethylene terephthalate (PET), mylar, metal foil, polyester, polyolefin, polycarbonate, polyolefin, polystyrene, polyacrylamide, polymethacrylate, poly(methyl)methacrylate, polyimide, polyester, polyethylene terephthalate, polybutylene terephthalate, polyvinylchloride, or a combination thereof. In one embodiment, the three-layer laminate 303 is made from polyethylene terephthalate (PET). In one embodiment, the bottom portion 200' and top portion 300' are made from heat-sealable materials. The layers of the three-layer laminate 303 may be adhered together using a suitable adhesive, such as a pressure sensitive adhesive. Examples of suitable pressure sensitive adhesives include silicone polyurea (SPU), acrylics, silicones, and rubber-based adhesives. Alternatively, the layers of the three-layer laminate 303 may be adhered together using a suitable structural adhesive such as acrylic, cyanoacrylate, epoxy, polyurethane, or a mixture thereof.

The films used to prepare the bottom portion 200' and top portion 300' may independently have any suitable thickness, such as 0.5 mil or greater, 1 mil or greater, 2 mil or greater, 4 mil or greater, or 6 mil or greater. The thickness of the films may be 100 mil or less, 50 mil or less, 40 mil or less, 25 mil or less, 10 mil or less, or 5 mil or less. In some embodiments, the three-layer laminate 303 is made from layers independently having a thickness of 4 mil or greater, 6 mil or greater, 8 mil or greater, or 10 mil or greater. The three-layer laminate 303 may be made from layers independently having a thickness of 100 mil or less, 50 mil or less, 40 mil or less, 25 mil or less, 10 mil or less, or 5 mil or less. The layers of the three-layer laminate 303 may have the same thickness or may have different thicknesses from one another. In one embodiment, each of the layers of the three-layer laminate 303 independently have a thickness ranging from 2 mil to 50 mil, from 5 mil to 40 mil, or from 10 mil to 30 mil. Each of the layers (the lumen layer 330, the top layer 331, and the bottom layer 332) may further include sub-layers, where the layer itself is prepared from multiple sub-layers.

The layers of the three-layer laminate 303 and the various features in the layers may be prepared by any suitable method. For example, the layers of the three-layer laminate 303 may be prepared by punching, laser cutting, or etching the features onto the respective layers before laminating the layers together. In one embodiment, the lumen layer 330 is prepared by laser cutting, punching, or etching the lumen path 333 onto a film, the top layer 331 is prepared by laser cutting, punching, or etching the opening 131' onto a second film, and the bottom layer 332 is prepared by laser cutting, punching, or etching the opening 132' onto a third film. The first, second, and third films may then be laminated or bonded together (e.g., using an adhesive) such that the lumen layer 330 is sandwiched between the top layer 331 and the bottom layer 332, and the opening 131' aligns with the first end 341 of the lumen path 333 and the opening 132' aligns with the second end 342 of the lumen path 333.

In the three-layer laminate 303, the channel hydraulic radius R130 is determined by the thickness T330 of the lumen layer 330 and the width W333 of the lumen path 333. The thickness T330 of the lumen layer 330 may be 4 mil or greater, 6 mil or greater, 8 mil or greater, or 10 mil or greater. The thickness T330 of the lumen layer 330 may be 100 mil or less, 50 mil or less, 40 mil or less, 25 mil or less, or 10 mil or less. The width W333 of the lumen path 333 may be adjusted to arrive at a desired hydraulic radius R130. The size (e.g., diameter or cross dimension) of the openings 131', 132' may be selected to accommodate the size of the lumen path 333. In some embodiments, the openings 131', 132' may have a diameter or cross dimension of 1 mm or greater, 2 mm or greater, or 3 mm or greater. The openings 131', 132' may have a diameter or cross dimension of 10 mm or less, 7 mm or less, 5 mm or less, or 4 mm or less.

According to some embodiments, the sterilization test pack 1 includes only a single indicator compartment 110. The single indicator compartment 110 may house one or more indicators, such as a biological indicator 401, a chemical indicator 402, or both.

Figure 7:
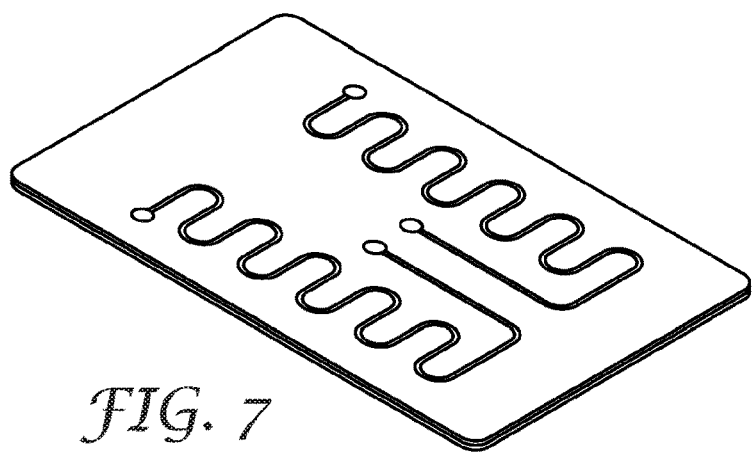
FIG. 7 is a perspective view of a layered structure of a sterilization test pack according to an embodiment.

According to some embodiments, the sterilization test pack 1 includes only a single channel 130 connecting the indicator compartment to the exterior of the pack. In an alternative embodiment, the sterilization test pack 1 includes two or more channels 130. The two or more channels may be closed by a closure (e.g., a seal, tab, or sticker), which may be selectively removed or opened by a user. The channels 130 may be constructed or configured to have different dimensions and thus different diffusivity $L_D$, allowing the user to select a level of diffusivity most suited for the intended sterilization conditions. An exemplary layered structure 1303 is shown in FIG. 7. For example, the sterilization test pack 1 may include a first channel 1331 having a first level of diffusivity $L_D$ suitable for one type of sterilization cycle (e.g., a gravity cycle), and a second channel 1332 having a second level of diffusivity $L_D$ suitable for another type of sterilization cycle (e.g., a pre-vacuum cycle). The different levels of diffusivity $L_D$ may be achieved by varying one or more of the parameters that affect diffusivity, such as hydraulic radius or length. Prior to use, the exterior openings of both channels may be closed by a closure. The user may prepare the sterilization test pack by selectively opening one of the channels by removing or opening the closure. The channels may be independently formed, each having a separate exterior opening and compartment opening, or may converge to share a common compartment opening.

In one embodiment, the sterilization test pack 1 includes a plurality of channels 130. The plurality of channels 130 may be formed by using a micro-structured film. For example, the top portion 300 may include a micro-structured film with a plurality of channels formed between a micro-structured side of the film and the flat portion 201 of the bottom portion 200. Suitable micro-structured films are known from, for example, U.S. patent numbers U.S. Pat. Nos. 5,728,446 and 5,514,120. In use, the shortest path length formed from the edge of the micro-structured film to the indicator compartment 110 would likely provide the path of least resistance and thus act as the channel 130 for the sterilant.

In the various embodiments of this disclosure, any suitable indicators, including biological and/or chemical indicators, may be used. For example, a biological indicator exhibiting a desired resistance to the sterilant may be used. The resistance of the biological indicator may contribute to the overall sterilization test pack resistance. Thus, depending on the sterilization cycle conditions used, a lower or higher resistance biological indicator may be selected. Similarly, a chemical indicator that indicates reaching of a desired sterilization condition (e.g., a certain sterilization temperature) may be selected.

Typical steam sterilization temperatures range from 121° C. to 135° C. Further, typical sterilization cycles include gravity cycles and pre-vacuum steam cycles. Due to the differences between these two types of cycles, namely gravity and pre-vacuum, different indicators and materials may be selected to make the sterilization test pack for the respective cycle type.

EXAMPLES

These examples are merely for illustrative purposes only and are not meant to be limiting on the scope of the appended claims. All parts, percentages, ratios, etc. in the examples and the rest of the specification are by weight, unless noted otherwise. The following abbreviations are used here: m=meter; cm=centimeter; mm=millimeter; $cm^2$=square centimeter; $cm^3$=cubic centimeter.

The performance of various types of sterilization test packs was tested and evaluated against a control. The test packs were tested using a gravity cycle and a pre-vacuum cycle.

Preparatory Example, Test Pack Type A

Test Pack Type A was prepared using a 2-mil (0.002 inches) thick heat-sealable PET film (PERFECSEAL® #35881-E available from Bemis Company, Inc. in Neenah, WI) to create an enclosed pouch for housing a biological and a chemical indicator, and a film-based lumen channel.

The 2-mil PET film pouch was sealed peripherally using a handheld direct heat sealer. The heat seal width was between 0.25-0.5 inches, which created an adequate seal that could withstand the autoclave temperature, pressure, and vacuum conditions. The rectangular PET film pouches were sealed on three (3) sides. The fourth side of the PET film pouch necessarily remained open to allow for the eventual placement of the internal biological and chemical indicator. The volume of the otherwise flat PET film pouch was determined by filling the pouch with water and pouring its filled contents into a graduated cylinder. A handheld cork-borer was used to create a 0.125 inch diameter hole in one of the two PET film layers. This 0.125 inch diameter hole is where the lumen path would make fluid communication with the enclosed volume of the PET film pouch.

The film-based lumen channel component of Test Pack Type A was created by laminating multiple layers of SPU adhesive-coated PET film. The SPU adhesive was 2-mils (0.002 inches) thick, and the PET film was 10-mils (0.010 inches) thick. The top and bottom layers of the lumen channel component were made up of a single layer of PET film. The middle layer defining the lumen channel was made by stacking one or more layers of the PET film to vary the height. The adhesive-backed PET film was cut to shape using a laser cutter. A 0.125-inch diameter hole was laser-cut into the top and bottom layers of the lumen channel laminate, and these 0.125-inch diameter holes functioned as the steam inlet into the lumen channel and entrance into the enclosed PET film pouch. A lumen path was laser cut into the middle layer, defining the length, width, and height of the lumen channel. The number of stacked middle layers determined the lumen channel height. The laser-cut tortuous path in the middle layers defined the lumen length and lumen width. The lumen channel width and height were used to calculate an effective hydraulic radius of the lumen channel.

The bottom, middle, and top layers of the film-based lumen channel were dry laminated together by hand, and then pressed in a manual roller press to remove air bubbles in the adhesive bond line and to increase adhesion of the press-sensitive adhesive. The pressed film-based lumen laminate was then adhered to the PET film pouch, aligning the 0.125-inch diameter holes of the pouch and the bottom layer of the lumen channel component to fluidly connect the PET pouch volume to the lumen channel. The entire construction was then pressed using a manual roller to ensure adequate adhesion of the lumen channel to the underlying PET film pouch. A biological indicator and chemical indicator were inserted into the PET pouch and the remaining open side of the PET film pouch was heat sealed. The biological indicators were 3M™ ATTEST™ Biological Indicators, and the chemical indicators 3M™ COMPLY™ STERIGAGE™ Steam Chemical Integrators.

Test Pack Type A was similar to the test pack shown in FIG. 4. Samples 1-7 were of Type A, having dimensions shown in Table 1.

TABLE 1

Test Pack Type A.

| Test Pack Type A Sample | PET Pouch Volume (cm³) | Channel Height (mm) | Channel Width (mm) | Channel Hydraulic Rad. (mm) | Channel Length (cm) | Diffusivity (cm) |
| --- | --- | --- | --- | --- | --- | --- |
| 1 | 115 | 0.25 | 0.76 | 0.19 | 15.2 | 0.03 |
| 2 | 82  | 0.25 | 0.76 | 0.19 | 15.2 | 0.06 |
| 3 | 115 | 0.25 | 0.76 | 0.19 | 5.1  | 0.27 |
| 4 | 82  | 0.25 | 0.76 | 0.19 | 5.1  | 0.53 |
| 5 | 115 | 0.51 | 0.76 | 0.30 | 15.2 | 4.92 |
| 6 | 82  | 0.51 | 0.76 | 0.30 | 15.2 | 6.47 |
| 7 | 115 | 0.51 | 0.76 | 0.30 | 5.1  | 29.70 |

Preparatory Example, Test Pack Type B

Test Pack Type B was prepared in a similar manner to Test Pack Type A, except the indicator cavity volume was created using a thermo-formed polypropylene tray with a heat-sealable aluminum foil lidding material with a co-extruded polypropylene ("PP") sealant layer. The thermo-formed tray was made from a 30-mil (0.030 inches) thick PACUR® 7020 medical grade polypropylene film. The heat-sealable aluminum foil lidding was Bemis L5103 material. A hand-held cork-borer was used to create a 0.125-inch diameter hole in the aluminum foil lidding material to function as an inlet into the indicator cavity.

The lumen channel of Test Pack Type B was created in the same way as described for Test Pack Type A. The lumen channel laminate was dry laminated and pressed to the sealant side of the Bemis L5103 lidding material, being careful to align the 0.125-inch diameter holes. A biological indicator and chemical indicator were placed in the thermo-formed PP tray, and then a heated press was used to bond the Bemis L5103 lidding with adhered lumen channel to the underlying thermo-formed PP tray. The settings used to create the heat seal were 100-PSI pressure, 365° F. temperature, for a dwell time of 2.5 seconds using a heated flat plate. The biological indicators were 3M™ ATTEST™ Biological Indicators, and the chemical indicators 3M™ COMPLY™ STERIGAGE™ Steam Chemical Integrators.

Samples 8-10 were of Type B, having dimensions shown in Table 2 below.

TABLE 2

Test Pack Type B.

| Test Pack Type B Sample | PP Tray Volume (cm³) | Channel Height (mm) | Channel Width (mm) | Channel Hydraulic Rad. (mm) | Channel Length (cm) | Diffusivity (cm) |
| --- | --- | --- | --- | --- | --- | --- |
| 8  | 49 | 0.51 | 0.76 | 0.30 | 35.6 | 3.30 |
| 9  | 49 | 0.76 | 0.66 | 0.35 | 35.6 | 14.60 |
| 10 | 49 | 0.76 | 0.76 | 0.38 | 35.6 | 30.70 |

Preparatory Example, Test Pack Type C

Test Pack Type C had a thermo-formed polypropylene tray prepared in a similar manner to Test Pack Type B, except the lumen channel was formed directly into the thermo-formed polypropylene tray in the same thermo-forming operation step used to create the indicator cavity volume. The thermo-formed tray was made from a 30-mil (0.030 inches) thick PACUR® 7020 medical grade polypropylene film. The heat-sealable aluminum foil lidding was Bemis L5103 material. The lumen channel cross-section was enclosed by the thermo-formed polypropylene tray and the heat-sealable aluminum foil lidding. The thermo-formed lumen path had an exterior opening at the periphery of the tray and the lid, which functioned as the steam entrance and exit point of the test pack.

Test pack type C was similar to the test pack shown in FIG. 1A. Sample 11 was of Type C, having dimensions shown in Table 3.

TABLE 3

Test Pack Type C.

| Test Pack Type C Sample | PP Tray Volume ($cm^3$) | Channel Height (mm) | Channel Width (mm) | Channel Hydraulic Rad. (mm) | Channel Length (cm) | Diffusivity (cm) |
|---|---|---|---|---|---|---|
| 11 | 49 | 0.51 | 0.76 | 0.30 | 15.2 | 18.00 |

Preparatory Example, Test Pack Control

The test pack control was prepared in accordance with ANSI/AAMI ST79, using 16 clean, reusable, absorbent surgical towels, each of which is approximately 16 inches× 26 inches. The towels were pre-conditioned at room temperature (65° F. to 75° F., about 18° C. to 24° C.) with a relative humidity at least 35% for a minimum of two (2) hours prior to testing. Individual towels were first folded in thirds lengthwise by folding one third over the middle third and the other third under the middle third. Then, each towel was folded width-wise in half, resulting in a folded towel of approximate dimensions 9 by 9 inches. Sixteen (16) pre-folded towels were then stacked to form a 16-towel pack of approximate dimensions 9 by 9 by 6 inches, with the towel folds alternating between layers. Four (4) biological indicators and four (4) chemical indicators were placed in the geometric center of the 16-towel pack, between the eighth and ninth towel. The biological indicators were 3M™ ATTEST™ Biological Indicators. The chemical indicators 3M™ COMPLY™ STERIGAGE™ Steam Chemical Integrators. The 16-towel pack with indicators was then secured using autoclave indicator tape.

Figure 8:
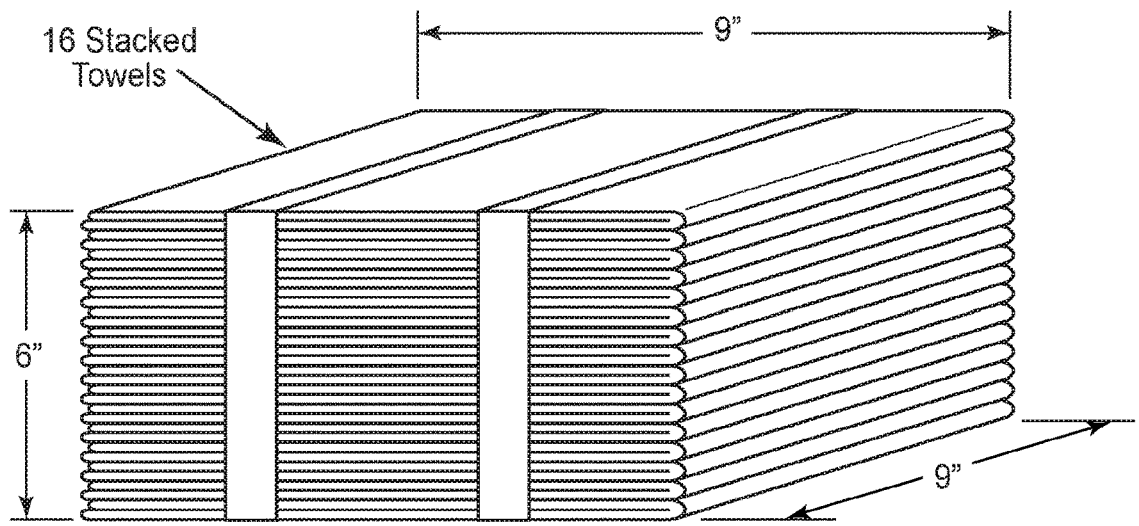
FIG. 8 is a schematic depiction of a control test pack used in the Examples.

The test pack control was similar to the test pack shown in FIG. 8. Sample 12 was the Test Pack Control, having overall dimensions of 9 by 9 by 6 inches and approximate dry weight of 3 pounds.

Test Methods

Method 1: Gravity Cycle

The evaluation of the lumen test packs (Types A, B, and C) alongside the control AAMI 16-towel pack in gravity steam sterilization cycles was performed in an AMSCO Eagle 3013C steam sterilizer. The gravity cycle performance evaluation included two main cycles, namely a 121° C. and 132° C. gravity steam sterilization cycle. At each temperature, the performance of the test packs was evaluated at two different exposure times, including a fractional exposure and complete cycle (i.e., full exposure). The gravity test cycle conditions are shown in Table 4 below.

TABLE 4

Sterilization Cycle Parameters.

| Gravity Cycle Parameter | 121° C. Test Cycle | 132° C. Test Cycle |
|---|---|---|
| SKELETON | GRAVITY | GRAVITY |
| STER TEMP | 121.1 | 132.2 |

TABLE 4-continued

Sterilization Cycle Parameters.

| Gravity Cycle Parameter | 121° C. Test Cycle | 132° C. Test Cycle |
|---|---|---|
| STER TIME | 20:00-30:00 | 11:00-15:00 |
| DRY TIME | 5:00 | 5:00 |
| DRY VAC | 0.0 inHg | 10.0 inHg |
| PURGE | 1:00 11p | 0:51 6p |
| FT | 108 C. | 108 C. |
| FP | 6 psig | 6 psig |
| STER CTRL | Drain | Drain |
| F0 SETPT | 00 OFF | 00 OFF |
| OVERDRIVE | 0.7 C. | 0.7 C. |
| OVERTEMP | 0.4 C. | 0.4 C. |
| UNDERTEMP | 1.0 C. | 1.0 C. |

In each gravity test cycle, one (1) 16-towel pack (Control) was run alongside three (3) or four (4) lumen test packs of Type A, B, or C. All test packs were placed on the bottom level of the sterilizer chamber and toward the front over the vessel drain.

Method 2: Pre-Vacuum Cycle

The evaluation of the lumen test packs (Types A, B, and C) alongside the control AAMI 16-towel pack (Control) in dynamic-air removal (i.e., pre-vacuum) steam sterilization cycles was performed in two different steam sterilizers, namely an AMSCO Eagle 3013C and Getinge 666-AC1 steam sterilizer. The 121° C., 132° C., and 134° C. pre-vacuum steam sterilization test cycles were performed in the AMSCO 3013C autoclave, while the 135° C. pre-vacuum test cycles were performed in the Getinge 666-AC1 autoclave. The pre-vacuum test cycle conditions are shown in Table 5 and Table 6. The fractional cycles included the lower exposure times and shorter pre-conditioning phases with fewer pulses.

TABLE 5

Sterilization Cycle Parameters.

| Pre-vacuum Cycle Parameter | 121° C. Test Cycle | 132° C. Test Cycle | 134° C. Test Cycle |
|---|---|---|---|
| SKELETON | PREVAC | PREVAC | PREVAC |
| STER TEMP | 121.1 | 132.2 | 134.0 |
| STER TIME | 20:00-30:00 | 2:30-4:00 | 1:00-3:30 |
| DRY TIME | 5:00 | 5:00 | 5:00 |
| DRY VAC | 0.0 inHg | 0.0 inHg | 0.0 inHg |
| PULSES | 2-4 | 2-4 | 2-4 |
| P1 | 26.0 psig | 26.0 psig | 26.0 psig |
| V1 | 10-24 inHg | 10-24 inHg | 10-24 inHg |
| P1 HOLD | 0:00 | 0:00 | 0:00 |
| V1 HOLD | 0:00 | 0:00 | 0:00 |
| PURGE | 1:00 6p | 1:00 6p | 1:00 6p |
| FT | 108 C. | 108 C. | 108 C. |
| FP | 6 psig | 6 psig | 6 psig |
| STER CTRL | Drain | Drain | Drain |
| F0 SETPT | 00 OFF | 00 OFF | 00 OFF |
| OVERDRIVE | 0.7 C. | 0.7 C. | 0.7 C. |
| OVERTEMP | 0.4 C. | 0.4 C. | 0.4 C. |
| UNDERTEMP | 1.0 C. | 1.0 C. | 1.0 C. |

TABLE 6

Sterilization Cycle Parameters.

| Cycle Parameter | Pre-vacuum 135° C. Test Cycle |
|---|---|
| PULS 1 + LVL | 2.068 BAR |
| PULS 2 + LVL | 2.068 BAR |
| PULS 3 + LVL | 2.068 BAR |
| PULS 1 − LVL | 0.672 BAR |
| PULS 2 − LVL | 0.328 BAR |
| PULS 3 − LVL | 0.328 BAR |
| PREVAC PULSES | 3 |
| PRE PLS RAMP NEG | 4.751/M |
| PRE PLS RAMP POS | 0.600/M |
| STER TRNSTN PNT | 2.5 C. |

TABLE 6-continued

Sterilization Cycle Parameters.

| Cycle Parameter | Pre-vacuum 135° C. Test Cycle |
|---|---|
| HEATUP PRESS RMP | 4.751/M |
| STER TEMP RAMP | 150.0/M |
| STERILIZE TEMP | 135.0 C. |
| STERILIZE TIME | 1:00-3:00 |
| RAMP DRYING | 4.751/M |
| DRY VAC DEPTH | 0.328 BAR |
| DRY TIME | 5:00 |
| POST PULSES | 0 |

In each pre-vacuum test cycle, one (1) 16-towel pack (Control) was run alongside three (3) or four (4) lumen test packs of Type A, B, or C. All test packs were placed on the bottom level of the sterilizer chamber and toward the front over the vessel drain.

Method 3: Evaluation of Test Pack Performance

Upon completion of each gravity and pre-vacuum test cycle, the biological indicators and chemical indicators were removed from the lumen test packs and 16-towel pack (Control). The biological indicators were incubated at 60° C. for 7-days to test for growth, and the run lengths of the STERIGAGE chemical indicators were measured and recorded. For each test cycle condition, the performance of the biological and chemical indicators in the 16-towel pack (Control) was compared to that of the lumen test packs of Type A, B, and C. In the fractional exposure cycle, the test pack Type A, B and C needed to show comparable performance to that of the 16-towel pack (Control). This means an equal to or greater number of surviving biological indicators and/or comparable run length on the SteriGage moving front chemical integrators. In the complete test cycles, where the cycles run to completion, the test pack Type A, B, and C needed to show adequate kill of the biological indicators and "Accept" results for the chemical indicators. The comparison between the test pack Type A, B, and C performance to that of the 16-towel pack (Control) are shown in Table 7.

Results

Table 7 shows the performance of the test pack samples in gravity and pre-vacuum steam sterilization cycles compared to the performance of the same biological indicators and chemical indicators in a 16-towel pack (Control).

TABLE 7

Test Pack Performance.

| Sample ID (Type) | Diffusivity (cm) | Gravity 121° C. | Prevac 121° C. | Gravity 132° C. | Prevac 132° C. | Prevac 134° C. | Prevac 135° C. |
|---|---|---|---|---|---|---|---|
| Sample 1 (A) | 0.03 | Hot | Hot | Hot | ADQ | ADQ | ADQ |
| Sample 2 (A) | 0.06 | Hot | Hot | Hot | ADQ | ADQ | ADQ |
| Sample 3 (A) | 0.27 | Hot | Hot | Hot | ADQ | ADQ | ADQ |
| Sample 4 (A) | 0.53 | Hot | Hot | Hot | ADQ | — | — |
| Sample 8 (B) | 3.30 | Hot | — | — | — | — | ADQ |
| Sample 5 (A) | 4.92 | ADQ | ADQ | — | — | — | — |
| Sample 6 (A) | 6.47 | ADQ | ADQ | Cold | Cold | Cold | Cold |
| Sample 9 (B) | 14.60 | ADQ | ADQ | — | — | — | Cold |
| Sample 11 (C) | 18.00 | ADQ | ADQ | ADQ | Cold | Cold | Cold |
| Sample 7 (A) | 29.70 | ADQ | ADQ | — | ADQ | — | Cold |
| Sample 10 (B) | 30.70 | ADQ | ADQ | — | — | — | Cold |
| Sample 12 (Control) | n/a | ADQ | ADQ | ADQ | ADQ | ADQ | ADQ |

Table 7 Legend:
Cold = Indicates insufficient resistance to meet 16-towel pack (Type C) equivalence
ADQ = Indicates adequate 16-towel pack (Type C) equivalence and adequate kill in complete cycle
Hot = Indicates resistance is too high, and adequate kill is not achieved in complete cycle.

It was observed that creating a lumen-based test pack to match the performance of the 16-towel pack (Control) across the entire temperature range of 121° C. to 135° C. in gravity and dynamic-air removal (i.e., pre-vacuum) steam sterilization cycles is non-trivial. In general, higher resistance to steam penetration in the high temperature pre-vacuum steam sterilization cycles is helpful to match the 16-towel pack performance. Conversely, less resistance is helpful to match the 16-towel pack performance in the low-temperature gravity steam cycles.

It was observed that the test pack indicator cavity volume, lumen channel length, and lumen channel radius play a significant role in providing resistance to steam penetration. Additionally, the extent to which these variables affect the test pack resistance to steam penetration varies with the steam cycle type, namely gravity or dynamic-air removal (i.e., pre-vacuum). In general, it was observed that test pack resistance to steam penetration increases as lumen length increases, lumen channel cross-section decreases, and indicator cavity volume increases.

While performance in a certain type of sterilization cycle is not limited to a test pack type, some of the aspects of the test packs were found suitable for a given cycle type. Sample 11 is an example of a lumen test pack construction particularly suitable for gravity steam cycles. Samples 1, 2, 3, and 8 are examples of lumen test pack constructions particularly suitable for dynamic-air removal (i.e., pre-vacuum) steam cycles.

The resistance of the test pack to steam penetration may also be influenced by the selection of the biological indicator. However, if a biological indicator of inherently lower resistance was used to repeat this evaluation, the comparative performance between the test pack Type A, B, and C and the 16-towel pack (Control) would not change. This is because the same indicators are used in all the samples. However, the test packs that perform "hot" in the lower-temperature gravity cycles, for example, would potentially show adequate kill in complete cycles due to the lower resistance of the biological indicator. Essentially, the inherent resistance of the biological indicator shifts the resistance of the entire test pack assembly up and down, in equal proportion, for both the test pack types (lumen and 16-towel pack). The resistance of the assembly can be analogized to an electrical circuit, where the biological indicator and lumen test pack are essentially two resistors in series, and increasing the resistance of the indicator increases the resistance of the pack as a whole. This also holds for the 16-towel pack, where the biological indicator and stack of absorbent towels are two (2) resistors in series.

Test Pack Type B with Lower Resistance Indicator

To test the impact of a lower-resistance biological indicator on the overall performance of the test pack, a series of additional Type B test packs were assembled according to Sample 8 above, using 3M™ ATTEST™ Biological Indicators with lower resistance.

Indicator resistance can be characterized using the D-value. The term "D-value" or "decimal reduction value" refers to the time required to achieve inactivation of 90% of a population of test organisms (also known as a 1 log reduction). The D-value may be expressed in minutes. The D-values of the biological indicators was 1.7 minutes at 121° C. The lower Test D-value indicates inherently lower resistance of the biological indicator.

The modified sample 8 with lower resistance biological indicator was designated "Sample 8L." Table 8 shows the performance of Sample 8L in a complete 121° C./30-minute gravity cycle. The performance of the Sample 8 test pack and 16-towel pack (type C) are shown again for comparison.

TABLE 8

Test Pack Performance

| Sample ID (Type) | Diffusivity (cm) | Gravity 121° C. | Prevac 121° C. | Gravity 132° C. | Prevac 132° C. | Prevac 134° C. | Prevac 135° C. |
|---|---|---|---|---|---|---|---|
| Sample 8L (B) | 3.30 | ADQ | — | — | — | — | — |
| Sample 8 (B) | 3.30 | Hot | — | — | — | — | ADQ |
| Sample 12 (Control) | n/a | ADQ | ADQ | ADQ | ADQ | ADQ | ADQ |

Table 8 Legend:
Cold = Indicates insufficient resistance to meet 16-towel pack (Type C) equivalence
ADQ = Indicates adequate 16-towel pack (Type C) equivalence and adequate kill in complete cycle
Hot = Indicates resistance is too high, and adequate kill is not achieved in complete cycle.

Whereas Sample 8 exhibited resistance that was too high in the 121° C. gravity cycle (designated "Hot" in TABLE 8), it was observed that Sample 8L with the lower-resistance biological indicator showed adequate performance with 16-towel pack (Control) equivalence and adequate kill in the complete cycle. While the Sample 8L test packs with lower-resistance biological indicators were not explicitly tested across the entire 121° C.-135° C. steam sterilization cycle range, it can be assumed that the relative resistance comparison between Sample 8L test pack and the 16-towel pack (Control) with the same lower-resistance biological indicators would not change. In this way, one could deduce that Sample 8L could perform adequately across the entire 121° C.-135° C. steam sterilization cycle range.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. It should be understood that this disclosure is not intended to be unduly limited by the illustrative embodiments and examples set forth herein and that such examples and embodiments are presented by way of example only with the scope of the disclosure intended to be limited only by the claims set forth here.

The invention claimed is:

1. A sterilization test pack comprising:
a shell defining an indicator compartment having a volume;
a channel extending between a compartment opening and an exterior opening, the channel being in fluid communication with the indicator compartment through the compartment opening and surrounding atmosphere being in fluid communication with the channel through the exterior opening such that the indicator compartment is in fluid communication with the surrounding atmosphere through the channel, the channel having a length measured between the compartment opening and the exterior opening and a hydraulic radius along the length; and
an indicator disposed in the indicator compartment,
a ratio of the compartment volume to the channel hydraulic radius ranging from 1000 $cm^2$ to 8000 $cm^2$.

2. The sterilization test pack of claim 1, wherein the shell comprises a top portion and a bottom portion.

3. The sterilization test pack of claim 2, wherein the top and bottom portions comprise polymeric film forming a pouch.

4. The sterilization test pack of claim 1, wherein the shell comprises a support element constructed to receive the indicator and to immobilize the received indicator within the indicator compartment.

5. The sterilization test pack of claim 1, wherein the sterilization test pack comprises only a single indicator compartment and a single channel.

6. The sterilization test pack of claim 1, wherein the sterilization test pack comprises two or more channels, each channel extending from an exterior opening to a compartment opening and providing a fluid connection between the indicator compartment and the surrounding atmosphere.

7. The sterilization test pack of claim 6, wherein the two or more channels comprise a first channel providing a first diffusivity and a second channel providing a second diffusivity different from the first diffusivity, and a closure configured to selectively close or open at least one of the first and second channels.

8. A sterilization test pack comprising:
a shell defining an indicator compartment having a volume;
a channel extending between a compartment opening and an exterior opening, the channel being in fluid communication with the indicator compartment through the compartment opening and surrounding atmosphere being in fluid communication with the channel through the exterior opening such that the indicator compartment is in fluid communication with the surrounding atmosphere through the channel, the channel having a length measured between the compartment opening and the exterior opening and a hydraulic radius along the length; and
an indicator disposed in the indicator compartment,
the sterilization test pack exhibiting a diffusivity ($L_D$) of 0.02 cm to 50 cm.

9. The sterilization test pack of claim 8, wherein the length of the channel is 30 mm or greater.

10. The sterilization test pack of any claim 8, wherein a ratio of the compartment volume to the channel hydraulic radius is 1000 $cm^2$ or greater.

11. The sterilization test pack of claim 8, wherein the shell comprises a top portion and a bottom portion and wherein the top and bottom portions comprise polymeric film forming a pouch.

12. The sterilization test pack of claim 8, wherein the shell comprises a support element constructed to receive the indicator and to immobilize the received indicator within the indicator compartment.

13. The sterilization test pack of claim 8, wherein the sterilization test pack comprises only a single indicator compartment and a single channel.

14. The sterilization test pack of claim 8, wherein the sterilization test pack comprises two or more channels, each channel extending from an exterior opening to a compartment opening and providing a fluid connection between the indicator compartment and the surrounding atmosphere.

15. The sterilization test pack of claim 14, wherein the two or more channels comprise a first channel providing a first diffusivity and a second channel providing a second diffusivity different from the first diffusivity, and a closure constructed to selectively close and open the first and second channels.

16. A sterilization test pack comprising:
a shell defining an indicator compartment having a volume of 15 $cm^3$ to 300 $cm^3$;
a channel extending between a compartment opening and an exterior opening, the channel being in fluid communication with the indicator compartment through the compartment opening and surrounding atmosphere being in fluid communication with the channel through the exterior opening such that the indicator compartment is in fluid communication with the surrounding atmosphere through the channel, the channel having a length of 30 mm to 1000 mm measured between the compartment opening and the exterior opening and a maximum hydraulic radius of 1.0 mm or less at any selected location along the length; and
an indicator disposed in the indicator compartment.

17. The sterilization test pack of claim 16, wherein the sterilization test pack exhibits a diffusivity ($L_D$) of 0.02 cm to 50 cm.

18. The sterilization test pack of claim 16, wherein the shell comprises a support element constructed to receive the indicator and to immobilize the received indicator within the indicator compartment.

19. The sterilization test pack of claim 16, wherein the sterilization test pack comprises two or more channels, each channel extending from an exterior opening to a compartment opening and providing a fluid connection between the indicator compartment and the surrounding atmosphere.

20. The sterilization test pack of claim 19, wherein the two or more channels comprise a first channel providing a first diffusivity and a second channel providing a second diffusivity different from the first diffusivity, and a closure constructed to selectively close and open the first and second channels.

* * * * *